US012790754B2

(12) United States Patent

Pyun

(10) Patent No.: US 12,790,754 B2

(45) Date of Patent: Nov. 10, 2026

(54) BIO-PROTECTIVE COMPOSITE MATERIALS, METHOD OF MANUFACTURING THE BIO-PROTECTIVE COMPOSITE MATERIALS, AND FACE MASK HAVING THE BIO-PROTECTIVE COMPOSITE MATERIALS

(71) Applicant: INDUSTRY-ACADEMIC COOPERATION FOUNDATION YONSEI UNIVERSITY, Seoul (KR)

(72) Inventor: Jae Chul Pyun, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 701 days.

(21) Appl. No.: 18/191,005

(22) Filed: Mar. 28, 2023

(65) Prior Publication Data

US 2023/0357990 A1 Nov. 9, 2023

(30) Foreign Application Priority Data

Mar. 31, 2022 (KR) ........................ 10-2022-0040196

(51) Int. Cl.

| | |
|---|---|
| ***D21H 17/67*** | (2006.01) |
| ***A41D 13/11*** | (2006.01) |
| ***B82Y 5/00*** | (2011.01) |
| ***B82Y 30/00*** | (2011.01) |
| ***D21H 21/36*** | (2006.01) |
| ***D21H 21/52*** | (2006.01) |
| ***D21H 27/08*** | (2006.01) |

(52) U.S. Cl.

CPC ....... *D21H 17/675* (2013.01); *A41D 13/1192* (2013.01); *D21H 21/36* (2013.01); *D21H 21/52* (2013.01); *D21H 27/08* (2013.01); *B82Y 5/00* (2013.01); *B82Y 30/00* (2013.01)

(58) Field of Classification Search

CPC .... A41D 13/1192; A41D 13/11; B82Y 30/00; B82Y 5/00; D21H 17/675; D21H 21/36; D21H 21/52; D21H 27/08; D21H 13/14; D21H 13/26; D21H 19/02; A62B 18/02; A62B 23/02; D06M 11/83

See application file for complete search history.

(56) References Cited

PUBLICATIONS

Flexible ZnO-Cellulose Nanocomposite for MultisourceEnergy Conversion (Year: 2011).*

Choi et al., "Recyclable, Antibacterial, Isoporous Through-Hole Membrane Air Filters with Hydrothermally Grown ZnO Nanorods" *Nanomaterials* 2021, 11:3381, 14 pages.

Li et al., "Fabrication and piezoelectric-pyroelectric properties of electrospun PVDF/ZnO composite fibers" *Mater. Res. Express* 2020, 7:095502, 8 pages.

Office Action issued in corresponding Korean Application No. 10-2022-0040196, dated Jul. 20, 2024 (English Translation provided).

* cited by examiner

*Primary Examiner* — Lynda Salvatore

(74) *Attorney, Agent, or Firm* — NORTON ROSE FULBRIGHT US LLP

(57) ABSTRACT

Disclosed is a bioprotective composite material. The bioprotective composite material includes a fiber network support, a seed layer for covering a surface of the fiber network support, and pyroelectric nanostructures protruding from the seed layer. Such bioprotective composite material generates a pyro-potential by a temperature change, and thus, has improved antibacterial and antiviral activities.

14 Claims, 13 Drawing Sheets

0

BIO-PROTECTIVE COMPOSITE MATERIALS, METHOD OF MANUFACTURING THE BIO-PROTECTIVE COMPOSITE MATERIALS, AND FACE MASK HAVING THE BIO-PROTECTIVE COMPOSITE MATERIALS

CROSS-REFERENCE TO RELATED APPLICATION

This application claims a benefit under 35 U.S.C. § 119(a) of Korean Patent Application No. 10-2022-0040196 filed on Mar. 31, 2022, on the Korean Intellectual Property Office, the entire disclosure of which is incorporated herein by reference for all purposes.

BACKGROUND

1. Field

The present disclosure relates to a bioprotective material having a direct sterilization ability against viruses, bacteria, and the like, a method for preparing the same, and a face mask including the same.

2. Description of Related Art

Infectious diseases caused by bacteria and viruses may rapidly spread globally. As observed in recent cases such as SARS in 2002, HINI influenza pandemic in 2009, and Ebola virus epidemic in 2014, the infectious diseases may have devastating consequences for human health, social communities, and the global economy. Recently, a public attention has been refocused by the COVID-19 pandemic. The COVID-19 pandemic is a contagious respiratory disease caused by SARS-CoV-2, and has infected 293,750,692 people and caused 5,454,131 deaths as of Jan. 6, 2022. Therefore, most countries have made it mandatory to wear face masks in public places to prevent rapid spread of COVID-19. The face mask is effective in blocking pathogens and lowering a risk of infection. However, the mask cannot provide direct sterilization and inactivation of the pathogens. Additionally, although antibacterial and antiviral drugs have been developed to target and kill specific bacterial and viral species, the pathogens gradually develop drug resistance in succession, which results in secondary infection. For example, because the SARS-CoV-2 virus mutates over time (i.e., delta and omicron mutations), COVID-19 is a pandemic emerged in 2019 and still ongoing, and increases risks of viral invasion and/or or reinfection. In this respect, there is an urgent need for a wearable material that may be incorporated into the face mask, may provide promising bioprotective functions, and may have good bactericidal capabilities.

Recent research has focused on a development of a bioprotective material that exhibits antibacterial and/or antiviral properties. Although underlying mechanism of sterilization and virus eradication actions of the bioprotective material is still unclear, oxidative stress caused by reactive oxygen species (ROS) is accepted as a major cause of cell and virus damage. Metal nanoparticles such as Ag and Cu have been extensively studied for sterilization properties thereof, and generally are applied in combination with a matrix support.

Metal nanoparticles cause the oxidative stress in nucleic acids by binding to a bacterial cell membrane or viral protein, disrupting an integrity of the cell or the virus, and generating the ROS. However, uncontrollable aggregation of the nanoparticles hinders application thereof. In addition, some metal nanoparticles have been reported to be toxic to humans and may permanently accumulate inside a human body, which causes human health problems. In addition to the metal nanoparticles, organic peptide substances such as chitosan, nisin, and the like may bind to cell walls, causing cell division and further oxidative damage to the cells. Therefore, the organic peptide substances have been proposed as antibacterial substances. In addition, the organic substances exhibit virus eradication properties by directly binding to viral capsid protein and blocking viral adsorption to a host cell. However, the organic substances generally exhibit low stability and low solubility in a biological fluid, so that application thereof is limited.

Several studies have reported that the ROS generation may be triggered by harvesting thermal energy, and this strategy is based on a thermoelectric or pyroelectric effect of the substance. When heat is an abundant, common, and readily available source of energy (e.g., geothermal and solar heat, hot water, computer heat, exhaust from a vehicle and a power plant, and the like), the thermal energy harvesting is sustainable and economical means for converting the heat into a desired form of energy. A thermoelectric material may convert the thermal energy into electricity based on the Seebeck effect, where a spatial temperature gradient exists. However, in an environment where the temperature is spatially uniform, the thermoelectric material is no longer useful for the energy conversion.

SUMMARY

A purpose of the present disclosure is to provide a bioprotective composite material having antibacterial and antiviral activities by generating a pyro-potential by a temperature change.

Another purpose of the present disclosure is to provide a method for preparing the bioprotective composite material.

Another purpose of the present disclosure is to provide a face mask having the bioprotective composite material and capable of exhibiting the antibacterial and antiviral activities via the pyro-potential generated by user's breathing.

Purposes in accordance with the present disclosure are not limited to the above-mentioned purpose. Other purposes and advantages in accordance with the present disclosure as not mentioned above may be understood from following descriptions and more clearly understood from embodiments in accordance with the present disclosure. Further, it will be readily appreciated that the purposes and advantages in accordance with the present disclosure may be realized by features and combinations thereof as disclosed in the claims.

A first aspect of the present disclosure provides a bioprotective composite material comprising: a fiber network support; a seed layer for covering a surface of the fiber network support; and pyroelectric nanostructures protruding from the seed layer and generating an instantaneous pyro-potential by a temperature change.

In one implementation of the first aspect, the fiber network support contains a fabric of polymer fibers.

In one implementation of the first aspect, the polymer fibers are made of a polyamide-based, polyimide-based, polypropylene-based, or polyethylene-based polymer material having hydrophilicity.

In one implementation of the first aspect, the seed layer is made of an inorganic material containing a metal element of a material constituting the pyroelectric nanostructures, and covers a surface of the polymer fibers constituting the fiber network support.

In one implementation of the first aspect, each of the pyroelectric nanostructures has a shape of a nanorod oriented in a direction protruding from the seed layer.

In one implementation of the first aspect, each of the pyroelectric nanostructures contains crystalline zinc oxide.

In one implementation of the first aspect, the pyroelectric nanostructures have an average diameter in a range from 50 to 400 nm and an average length in a range from 600 to 1500 nm.

A second aspect of the present disclosure provides a method for preparing a bioprotective composite material, the method comprising: immersing a fiber network support made of hydrophilic polymer fibers in a seed aqueous solution containing zinc ions and then annealing the fiber network support to form a seed layer made of a zinc-containing inorganic material on a surface of the polymer fibers; and growing zinc oxide nanorods on a surface of the seed layer via hydrothermal synthesis.

In one implementation of the second aspect, the hydrothermal synthesis is performed by maintaining the fiber network support with the seed layer formed thereon at a temperature in a range from 80 to 100° C. for 1.5 to 3 hours while immersed in a zinc oxide precursor solution.

In one implementation of the second aspect, the zinc oxide nanorods have an average diameter in a range from 50 to 400 nm and an average length in a range from 600 to 1500 nm.

A third aspect of the present disclosure provides a face mask comprising: a mask; and a bioprotective composite material coupled to the mask and including a fiber network support, a seed layer for covering a surface of the fiber network support, and pyroelectric nanostructures protruding from the seed layer.

In one implementation of the third aspect, the bioprotective composite material generates a pyro-potential by a temperature change caused by breathing of a user wearing the face mask.

In one implementation of the third aspect, deformation of the bioprotective composite material based on a facial curve of the user causes lattice deformation of the pyroelectric nanostructures.

According to the bioprotective composite material and the face mask including the same of the present disclosure, the bioprotective composite material may generate the pyro-potential via the temperature change caused by the user's breathing without using the external power, and may promote the reactive oxygen species (ROS) using the pyro-potential, so that the face mask may have the significantly improved antibacterial and antiviral activities.

In addition, when the bioprotective composite material is applied to the face mask, the polarization is improved by the lattice deformation of the pyroelectric nanostructures generated based on the facial curve of the user, so that the pyroelectric performance of the bioprotective composite material may be further improved.

In addition to the effects as described above, specific effects in accordance with the present disclosure will be described together with the detailed description for carrying out the disclosure.

DETAILED DESCRIPTIONS

Figure 1:
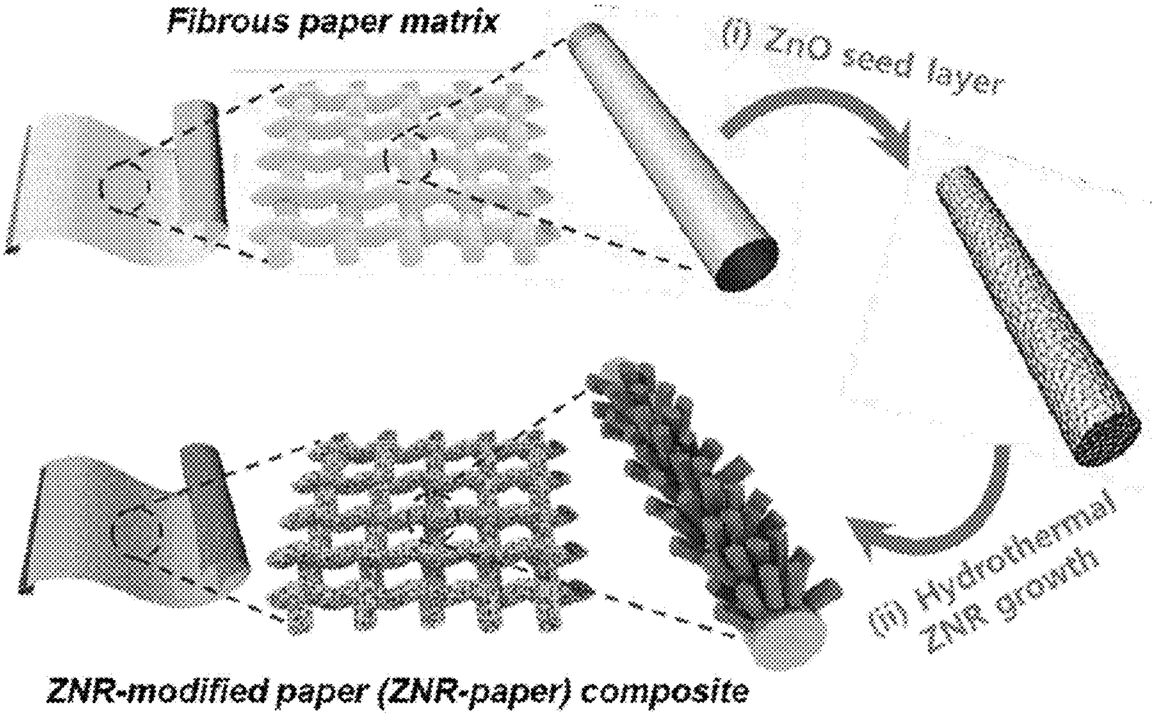
FIG. 1 is a view for illustrating an embodiment of a bioprotective composite material and a method for preparing the same according to an embodiment of the present disclosure.

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

A shape, a size, a ratio, an angle, a number, etc. disclosed in the drawings for illustrating embodiments of the present disclosure are illustrative, and the present disclosure may not be limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular embodiments only and is not intended to limit the present disclosure. As used herein, the singular forms "a" and "an" are intended to include the plural forms as well, unless the context clearly indicates otherwise. It will be further understood that the terms "comprise," "comprising," "include," and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D," this means C inclusive to D inclusive unless otherwise specified.

It will be understood that, although the terms "first," "second," "third," and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

It will be understood that when an element or layer is referred to as being "connected to," or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one example, when a certain embodiment may be implemented differently, a function or operation specified in a specific block may occur in a sequence different from that specified in a flowchart. For example, two consecutive blocks may be actually executed at the same time. Depending on a related function or operation, the blocks may be executed in a reverse sequence.

In descriptions of temporal relationships, for example, temporal precedent relationships between two events such as "after," "subsequent to," "before," etc., another event may occur therebetween unless "directly after," "directly subsequent" or "directly before" is not indicated.

The features of the various embodiments of the present disclosure may be partially or entirely combined with each other, and may be technically associated with each other or operate with each other. The embodiments may be implemented independently of each other and may be implemented together in an association relationship.

<Bioprotective Composite Material and Method for Preparing the Same>

FIG. 1 is a view for illustrating an embodiment of a bioprotective composite material and a method for preparing the same according to an embodiment of the present disclosure.

Referring to FIG. 1, the bioprotective composite material according to an embodiment of the present disclosure may include a fiber network support, a seed layer for covering a surface of the fiber network support, and pyroelectric nanostructures protruding from the seed layer.

The fiber network support may contain a fabric of polymer fibers. Accordingly, the fiber network support may have pores through which gases may pass, and may have flexibility capable of being bent based on a shape or deformation of a matrix to which it is applied.

In one embodiment, the fiber network support may be made of polymer fibers having hydrophilicity. For example, the polymer fibers may be formed of a polymer material such as polyamide, polyimide, polypropylene, or polyethylene.

The seed layer may be formed to cover the fiber surface of the fiber network support. The seed layer may be made of an oxide, a nitride, or the like containing a metal element of a material constituting the pyroelectric nanostructure. In one embodiment, when the pyroelectric nanostructures are made of a zinc oxide, the seed layer may be made of a zinc-containing oxide, for example, the zinc oxide.

In one embodiment, the seed layer may be formed to have a thickness that does not significantly limit the flexibility of the fiber network support. For example, the seed layer may be formed to have a thickness of several nm to several tens of μm.

In one embodiment, the seed layer may be formed by immersing the fiber network support in a seed solution for a predetermined time and then annealing the fiber network support. For example, when the pyroelectric nanostructures are made of the zinc oxide, the fiber network support may be immersed in an aqueous precursor solution containing zinc ions for about 0.5 to 1.5 hours and then annealed for about 0.2 to 1 hour at a temperature in a range from about 70 to 100° C. to form the seed layer with a high density on the polymer fibers. In this case, when the fiber network support is made of the polymer fibers having the hydrophilicity, the seed layer that uniformly covers the surface of the polymer fibers and has the high density may be formed.

The pyroelectric nanostructures may be formed to protrude from the seed layer, and may be made of a material having pyroelectricity capable of generating a temporary voltage by changing a polarized state based on a temperature change. For example, the pyroelectric nanostructures may be made of crystalline zinc oxide (ZnO), barium titanate ($BaTiO_3$), lithium niobate ($LiNbO_3$), lead zirconate titanate ($Pb[Zr_XTi_{1-X}]O_3$), and the like. For example, the pyroelectric nanostructures may be made of zinc oxide (ZnO) in a wurtzite phase.

In one embodiment, the pyroelectric nanostructures may have a nanorod structure grown in a direction substantially perpendicular to the surface of the seed layer. When the pyroelectric nanostructures have the nanorod structure regularly oriented with respect to the surface of the seed layer, a dipole moment induced during bending of the bioprotective composite material may be increased to increase the generated pyro-potential and to improve antibacterial and antiviral efficiency because of an increase in a surface area. For example, the pyroelectric nanostructures may have a nanorod shape having an average diameter in a range from about 50 to 400 nm and an average length in a range from about 600 to 1500 nm.

In one embodiment, the pyroelectric nanostructures may be formed via hydrothermal synthesis in the state in which the fiber network support on which the seed layer is formed is immersed in the precursor solution for the nanostructures. In this case, the nanorod structures oriented substantially perpendicular to the surface of the seed layer may be uniformly formed. In one embodiment, the pyroelectric nanostructures may be grown from the seed layer by maintaining the fiber network support on which the seed layer is formed in the state of being immersed in the precursor solution at a temperature in a range from about 80 to 100° C. for about 1.5 to 3 hours.

In one example, because the pyroelectric nanostructures grown in this way have a relatively sharp outer end, the pyroelectric nanostructures may mechanically destroy a cell membrane of the bacteria, thereby further improving an antibacterial ability thereof.

<Face Mask>

A face mask according to an embodiment of the present disclosure may include a mask and the bioprotective composite material attached or bonded to the mask.

Because a known mask may be applied to the mask without a limitation, a detailed description thereof will be omitted.

The bioprotective composite material may be attached to an outer surface of the mask or embedded inside the mask.

When the bioprotective composite material is bonded to the mask, the bioprotective composite material may be deformed based on a facial curve of a user, and as a result, lattice deformation of the pyroelectric nanostructures may be caused. Such lattice modification may enhance the polarization of the pyroelectric nanostructures, resulting in further enhancement of a pyroelectric performance of the bioprotective composite material.

In addition, a temperature change may be generated by a breathing cycle of inhalation and exhalation of the user wearing the face mask, so that the bioprotective composite material may generate the pyro-potential by itself without using external power. Accordingly, a reaction for generating the reactive oxygen species (ROS) from surrounding water ($H_2O$) and oxygen ($O_2$) may be promoted. In addition, antibacterial and antiviral activities may be enhanced by oxidative stress caused by the reactive oxygen species.

According to the bioprotective composite material and the face mask including the same of the present disclosure, the bioprotective composite material may generate the pyro-potential via the temperature change caused by the user's breathing without using the external power, which may be used to promote the generation of the reactive oxygen species (ROS), so that the face mask may have the significantly enhanced antibacterial and antiviral activities.

In addition, when the bioprotective composite material is applied to the face mask, the polarization is improved by the lattice deformation of the pyroelectric nanostructures caused by the user's face curve, so that the pyroelectric performance of the bioprotective composite material may be further improved.

Hereinafter, specific examples of the present disclosure will be described in detail. However, the following examples are merely some embodiments of the present disclosure, and the scope of the present disclosure is not limited to the following examples.

[Present Example 1]: Synthesis of ZNR Paper Composite

A simple two-step process was used for large-area fabrication of ZnO nanorods fixed onto nylon paper.

For a uniform growth of ZNR (the ZnO nanorods), first, a ZnO seed layer was deposited on a fiber surface of a nylon paper matrix with a thickness of 120 μm. To this end, the nylon paper was immersed in a zinc acetate dihydrate seed solution (0.01 M) at a room temperature for 1 hour, followed by annealing at 80° C. for 30 minutes to create the dense seed layer on the fiber surface of the nylon paper matrix.

Subsequently, the paper matrix on which the ZnO seed layer was deposited was transferred to an aqueous growth solution containing zinc nitrate hexahydrate (0.025 M) and hexamethylenetertramine (0.025 M) and maintained at 85° C. for 2 hours to synthesize the ZnO nanorods on the ZnO seed layer.

Subsequently, after the hydrothermal process, the synthesized ZNR paper composite was washed with water to remove residue and then completely dried.

[Present Example 2]: Manufacture of Face Mask

Upper and lower electrodes were formed by depositing Au films on both surfaces of the ZNR paper composite (an active area of 400 $mm^2$) via a plasma sputtering process using a shadow mask.

Subsequently, the ZNR paper composite on which the upper and lower electrodes were formed was disposed between copper (Cu) tapes, two external copper wires were connected to both the copper tapes, and then the composite was sealed with a Kapton tape to prevent damage to manufacture a pyroelectric element.

The pyroelectric element was attached to a portion of an outer surface of a commercial face mask adjacent to a user's nose to measure a pyroelectric signal generated by the user's breath.

Experimental Example 1

Figure 2A:
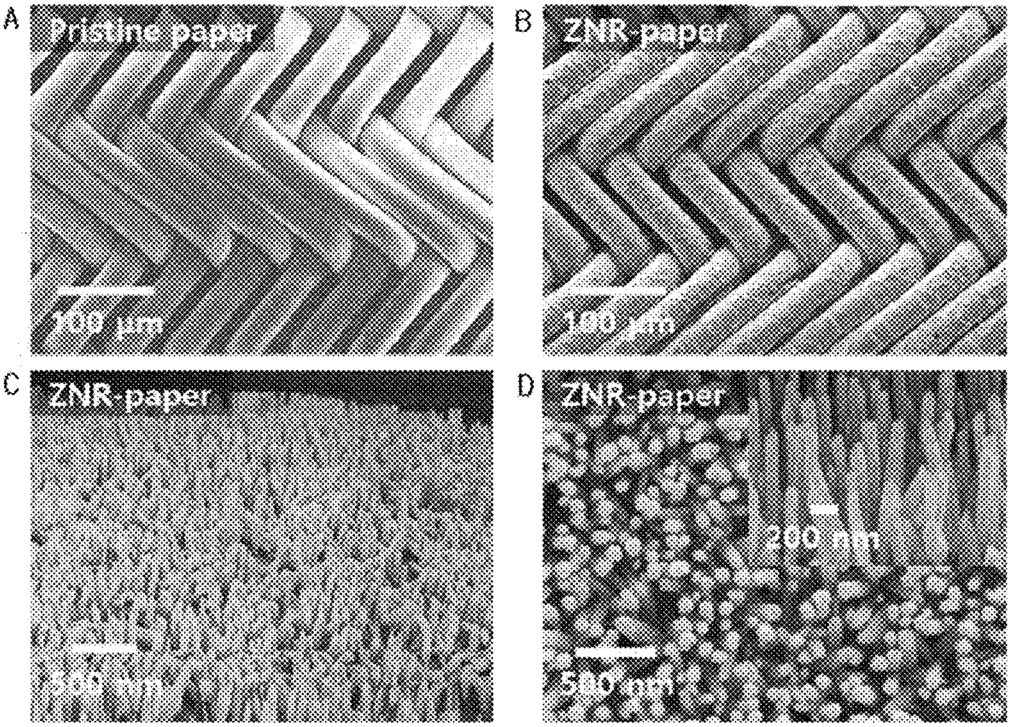
FIG. 2A shows images showing surface morphology of a nylon paper matrix A (upper left) and ZNR-papers B (upper right), C (lower left), and D (lower right)
Figure 2B:
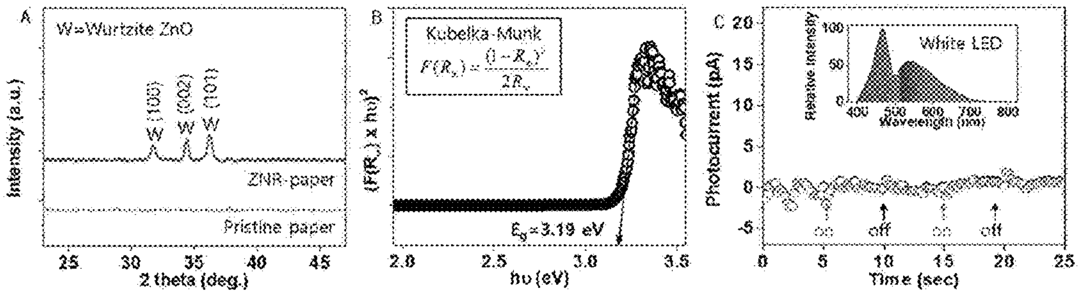
FIG. 2B shows graphs showing a HR-XRD pattern A (left) of the ZNR-paper, a band gap B (middle) determined using a tauc plot, and a photocurrent C (right) under a visible light irradiation condition.

FIG. 2A shows images showing surface morphology of a nylon paper matrix A (upper left) and ZNR-papers B (upper right), C (lower left), and D (lower right), and FIG. 2B shows graphs showing a HR-XRD pattern A (left) of the ZNR-paper, a band gap B (middle) determined using a tauc plot, and a photocurrent C (right) under a visible light irradiation condition.

Referring to FIGS. 2A and 2B together with FIG. 1, the nylon paper matrix has the fiber network having the pores and the large surface area. The fibers of the nylon paper exhibited a smooth surface that became significantly rougher when covered with the ZnO nanorods. The ZnO nanorods were vertically grown on the fibers of the nylon paper, and each had an average diameter of about 90.2 nm and a length of about 981.4 nm.

Unlike conventional piezoelectric/pyroelectric materials that mainly have brittleness, the ZNR-paper exhibited high deformability and recovery from mechanical stress because of the flexibility of the nylon paper matrix, from which it may be seen that the ZNR-paper may be applied to a wearable device. That is, the porous paper matrix not only provides an expanded surface area for fixing the ZnO nanorods, but also provides mechanical flexibility for application to the wearable device.

As shown in A (left) in FIG. 2B, the ZnO nanorods formed on the nylon paper fibers had a hexagonal wurtzite phase with non-central symmetry showing piezoelectric and pyroelectric anisotropic behaviors. A band gap energy of the ZnO nanorods evaluated using the tau plot of $(F(R_\infty)\times hv)^2$ for hv was 3.19 eV, which belongs to a UV area. Under repetitive turn-on and turn-off switching behavior conditions of a white LED irradiating the visible light in an area from 400 to 800 nm, no photoresponse was observed in the ZNR-paper composite.

Experimental Example 2

Figure 3A:
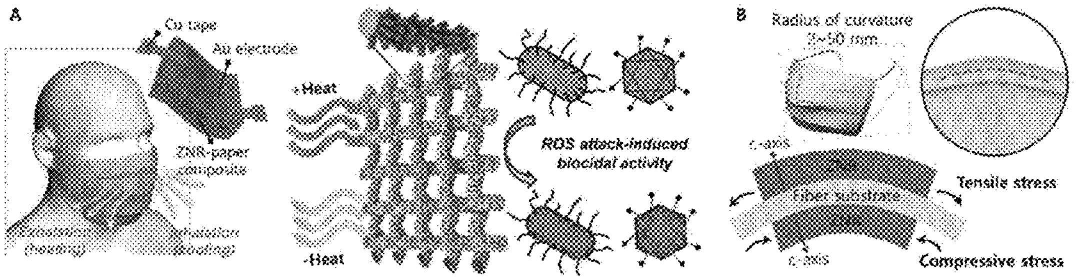
FIG. 3A is a diagram for conceptual illustration A (left) of breathing driving and self-electricity generation for antibacterial and antiviral activities of ZNR-paper and illustration B (right) of tensile and compressive stresses induced in the ZNR-paper attached to a curvature-changed face mask.
Figure 3B:
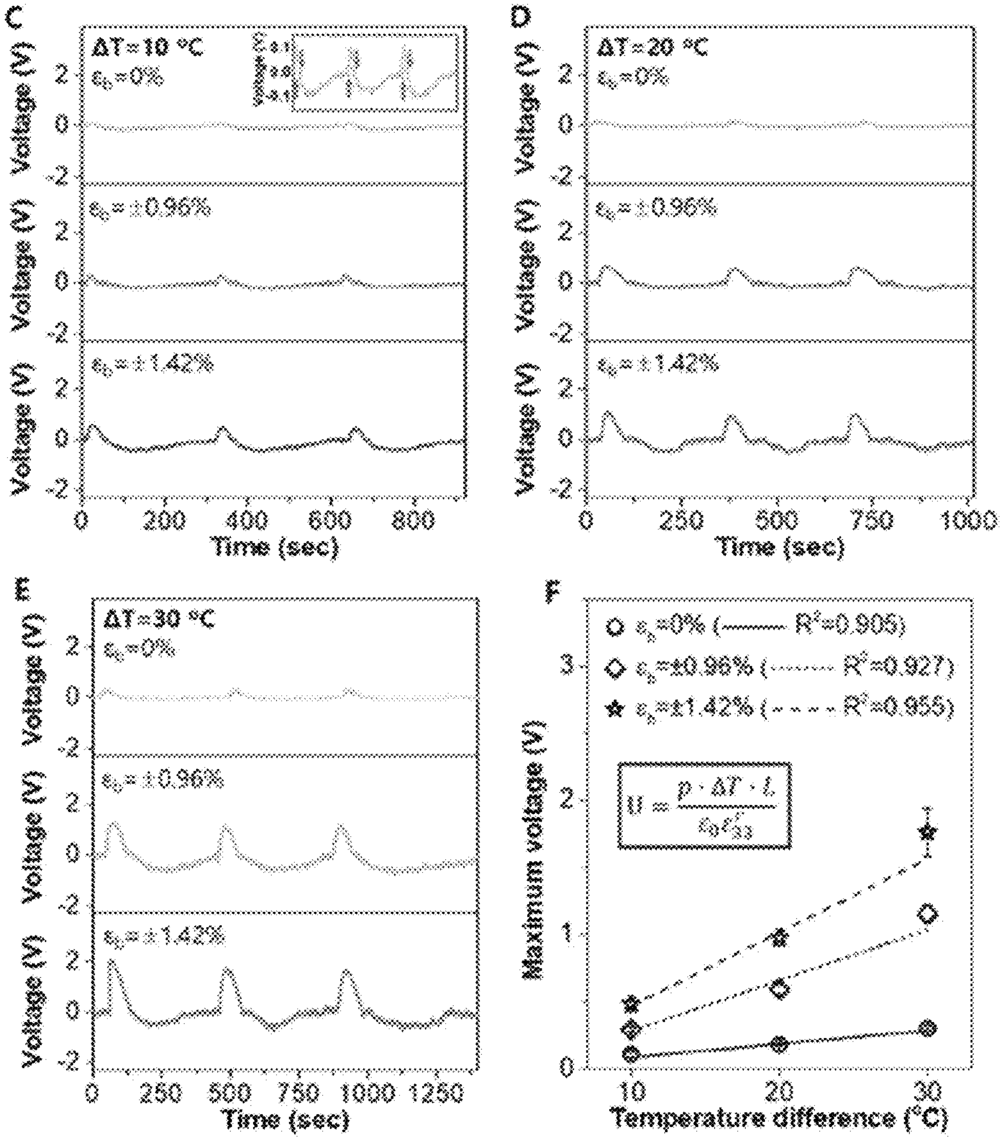
FIG. 3B shows graphs C (upper left), D (upper right), and E (lower left) showing pyroelectric open circuit voltages of an unstrained ZNR-paper ($\in_b={}_0$%) and strained ZNR-papers ($\in_b$=±0.96% and ±1.42%) under conditions of a temperature change (ΔT) of 10° C., 20° C., and 30° C., and a graph F (lower right) showing a linear relationship between a voltage and a temperature change.

FIG. 3A is a diagram for conceptual illustration A (left) of breathing driving and self-electricity generation for the antibacterial and antiviral activities of the ZNR-paper and illustration B (right) of tensile and compressive stresses induced in the ZNR-paper attached to the curvature-changed face mask. FIG. 3B shows graphs C (upper left), D (upper right), and E (lower left) showing pyroelectric open circuit voltages of an unstrained ZNR-paper ($\epsilon_b$=0%) and strained ZNR-papers ($\epsilon_b$=±0.96% and ±1.42%) under conditions of a temperature change (ΔT) of 10° C., 20° C., and 30° C., and a graph F (lower right) showing a linear relationship between the voltage and the temperature change.

Referring to FIGS. 3A and 3B, the temperature change over time may be caused by the user's breathing cycle consisting of the exhalation and the inhalation. Such temperature change may create a net change in a surface polarity of the ZnO nanorods and the pyroelectric potential resulted therefrom. The pyroelectric potential may consequently tilt electromagnetic band edges of the ZnO nanorods, which may positively affect a redox reaction for the generation of the ROS that are toxic to bacteria and viruses. On the other hand, the face mask has a strong curvature, especially in an area close to the nose, so that when attaching the ZNR paper to the outer surface of the mask, as shown in B (right) in FIG. 3A, an in-situ bending stress is applied to the ZnO nanorods grown to orient preferentially along a c-axis and having piezoelectric properties. Specifically, mechanical bending of the ZNR-paper composite applies a tensile stress to ZnO nanorods on a convex surface such that the ZnO nanorods are compressively strained along the c-axis, whereas applies a compressive stress to ZnO nanorods on a concave surface such that the ZnO nanorods are tensile strained along the c-axis. The lattice deformation of the ZnO nanorods induced by the bending may improve the polarization of the ZnO nanorods, and as a result, the pyroelectric performance of the ZnO nanorods may be further improved. Therefore, before demonstrating effectiveness of the ZNR-paper against the bacteria and the viruses, an effect of bending on pyroelectric properties of the ZNR-paper was investigated.

$$\epsilon_b = \frac{t}{2R} \quad \text{[Formula 1]}$$

$$R = \frac{L}{2\pi\sqrt{\frac{\Delta L}{L} - \frac{\pi^2 t^2}{12L^2}}} \quad \text{[Formula 2]}$$

In Formulas 1 and 2, t, R, L, and ΔL represent a substrate thickness, a radius of curvature, a substrate length, and a length reduced by the bending, respectively.

Calculated $\epsilon_b$ values corresponding to ΔL and R are listed in Table 1.

TABLE 1

| L (mm) | ΔL (mm) | R (mm) | $\epsilon_b$ (%) |
|---|---|---|---|
| 20 | 1 | 14.24 | 0.43 |
| 20 | 2 | 10.07 | 0.61 |
| 20 | 3 | 8.22 | 0.74 |
| 20 | 4 | 7.12 | 0.86 |
| 20 | 5 | 6.36 | 0.96 |
| 20 | 6 | 5.81 | 1.05 |
| 20 | 7 | 5.38 | 1.13 |
| 20 | 8 | 5.03 | 1.21 |
| 20 | 9 | 4.74 | 1.29 |
| 20 | 10 | 4.50 | 1.35 |
| 20 | 11 | 4.29 | 1.42 |
| 20 | 12 | 4.11 | 1.48 |
| 20 | 13 | 3.95 | 1.54 |
| 20 | 14 | 3.80 | 1.60 |
| 20 | 15 | 3.67 | 1.66 |

For the ZNR-paper, when the radii of curvature were 6.36 mm and 4.29 mm, $\epsilon_b$ values were evaluated to be 0.96% and 1.42%, respectively.

As shown in C (upper left) to E (lower left) in FIG. 3B respectively showing pyroelectric voltages of 0%-strained ZNR-paper, 0.96%-strained ZNR-paper, and 1.42%-strained ZNR-paper under conditions of the temperature change (ΔT) of the different magnitudes of 10° C., 20° C., and 30° C., the pyroelectric voltage of the ZNR-paper increased with the increasing temperature change. In addition, the strained ZNR-paper exhibited a significantly increased pyroelectric signal compared to the ZNR-paper unstrained for all ΔT. Specifically, an output voltage of the 1.42%-strained ZNR-paper was increased by 5.38 times and 1.53 times, respectively, compared to those of the 0%-strained ZNR-paper and the 0.96%-strained ZNR-paper for ΔT of 30° C. In addition, as shown in F (lower right) in FIG. 3B, an electrical response of the ZNR paper to the temperature change was linearly changed. A pyroelectric constant $p_{33}$ determined using Formula 2 below may explain a theoretical pyroelectric voltage U for the given temperature change ΔT.

$$U = \frac{p_{33} \cdot \Delta T \cdot L}{\epsilon_0 \epsilon_{33}^{T}} \quad \text{[Formula 3]}$$

In Formula 3, $p_{33}$, L, and $$\epsilon_{33}^{T}\left( = \frac{\epsilon_{33}^{T}}{\epsilon_0}, 11\right)$$

respectively denote the pyroelectric constant, a length, and a relative permeability along the c-axis of the ZnO nanorods, and $\in_0$ denotes a vacuum permeability ($8.85\times10^{-12}$ $Pm^{-1}$).

In the ZNR-paper composite, magnitudes of $p_{33}$ calculated based on the L value of the ZnO nanorods (a length of 0.98 μm) were 3.60 and 5.80 $\mu Cm^{-2}K^{-1}$ for the 0.96%-strained ZNR paper and the 1.42%-strained ZNR paper, respectively, which were increased by 3.67 times and 5.92 times, respectively, compared to the unstrained ZNR paper.

In some previous studies, it was reported that, even in an undoped state, because of a screening effect of intrinsic free charge carriers, pyroelectric and piezoelectric output voltages are significantly reduced in ZnO, $LiNbO_3$, and $PbZr_xTi_{1-x}O_3$ (PZT). Similarly, in a case of n-type ZnO nanorods immediately after the synthesis, positive charges of the pyro-potential was partially screened by free electrons. As a result, compared to a pyro-potential of the ZnO nanorods calculated using a theoretical pyroelectric constant (magnitude, 9.4 $\mu Cm^{-2}K^{-1}$), the output voltage was reduced by about $10^{-2}$ times or more.

It was shown that, in bent ZNR-paper with a significantly increased apparent $p_{33}$ value, a bending-induced strain has a beneficial effect on the pyroelectric performance based on the subsequent temperature change.

To structurally investigate a correlation between the bending strain and the pyroelectricity, HR-XRD analysis was performed. In addition, in terms of lattice deformation in ZnO nanorod crystals based on structural simulations, an origin of the pyroelectricity enhancement induced by the bending was investigated. In one example, a change in a structural parameter of the ZnO nanorods in the wurtzite phase based on an applied $\in_b$ was investigated using XRD data based on the Bragg's Law. A degree of the bending-induced lattice deformation was evaluated based on a Zn—O bond length and an O—Zn—O bond angle within a $ZnO_4$ tetrahedral unit and visualized using electromagnetic and structural analysis software.

Figure 4:
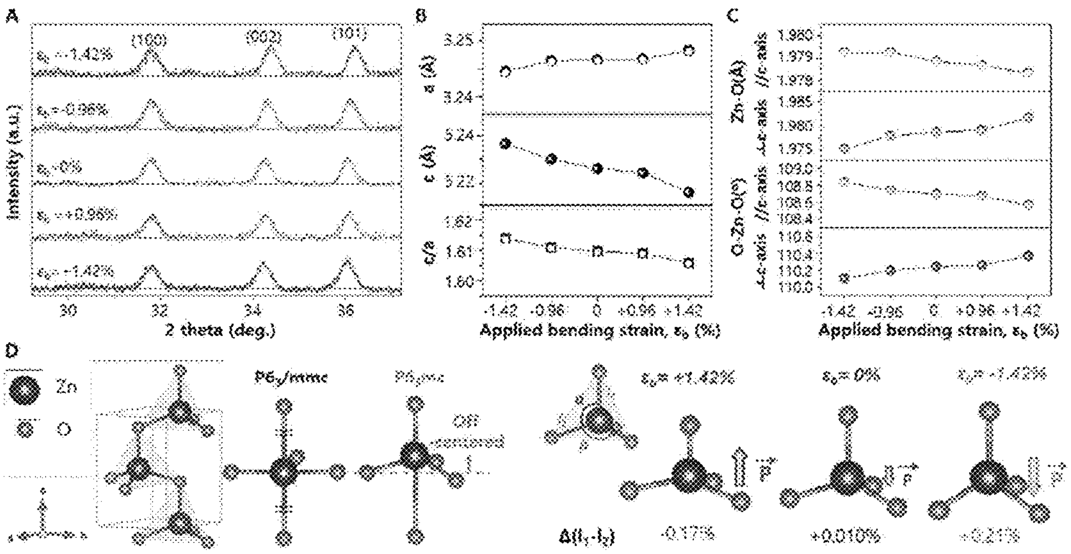
FIG. 4 shows a HR-XRD pattern A (upper left) for pre-strained ZNR-paper, a graph B (upper middle) showing a lattice constant and a c/a ratio based on an applied bending strain, a graph C (upper right) showing Zn—O bond lengths and O—Zn—O bond angles in a c-axis and in a direction perpendicular to the c-axis based on the applied bending strain, and a conceptual diagram D (lower) for illustrating lattice distortion of ZnO nanorods under tensile strain and compressive strain conditions.

FIG. 4 shows a HR-XRD pattern A (upper left) for pre-strained ZNR-paper, a graph B (upper middle) showing a lattice constant and a c/a ratio based on the applied bending strain, a graph C (upper right) showing Zn—O bond lengths and O—Zn—O bond angles in the c-axis and in a direction perpendicular to the c-axis based on the applied bending strain, and a conceptual diagram D (lower) for illustrating lattice distortion of the ZnO nanorods under the tensile strain and compressive strain conditions. In addition, Tables 2 and 3 are actual lattice parameters and structural parameters of the ZnO nanorods in the ZNR-paper composite.

TABLE 2

| Applied bending | Lattice constants | | |
|---|---|---|---|
| strain $\varepsilon_b$ (%) | a (Å) | c (Å) | c/a |
| −1.42 | 3.2446 | 5.2366 | 1.6139 |
| −0.96 | 3.2465 | 5.2301 | 1.6110 |
| 0 | 3.2467 | 5.2262 | 1.6097 |
| +0.96 | 3.2468 | 5.2244 | 1.6091 |
| +1.42 | 3.2483 | 5.2163 | 1.6059 |

TABLE 3

| Applied bending | Structural parameters | | | | |
|---|---|---|---|---|---|
| strain $\varepsilon_b$ (%) | $l_1$ (Å) | $l_2$ (Å) | l* (Å) | α (deg.) | β (deg.) |
| −1.42 | 1.9793 | 1.9752 | 3.2573 | 108.84 | 110.10 |
| −0.96 | 1.9791 | 1.9779 | 3.2508 | 108.74 | 110.20 |
| 0 | 1.9789 | 1.9787 | 3.2473 | 108.69 | 110.24 |
| +0.96 | 1.9787 | 1.9791 | 3.2457 | 108.67 | 110.26 |
| +1.42 | 1.9783 | 1.9817 | 3.2380 | 108.56 | 110.36 |

Referring to FIG. 4 and Tables 2 and 3, it was confirmed that the bending induced strain exists in the ZNR paper, and the ZNR paper is subjected to the bending stress and a change perpendicular to the c-axis.

As shown in B (upper middle) of FIG. 4, it was observed that a lattice parameter a of the ZnO nanorods gradually increases as $\in_b$ changes from the compressive bending strain to the tensile bending strain, which indicates expansion of a ZNR lattice in a lateral direction. On the other hand, it was observed that a lattice parameter c of the ZnO nanorods gradually decreases as $\in_b$ changes from the compressive bending strain to the tensile bending strain. It was observed that, compared to a lattice under the condition of no strain, a lattice of the ZnO nanorods under a condition of maximum compression/tension $\in_b$ (≈∓1.42%) contracted/expanded (−0.049%/+0.065%) along an a-axis while expanded/contracted (+0.19%/−0.20%) along the c-axis. In one example, anisotropic lattice deformations induced in-plane tensile strain and out-of-plane compressive strain in the ZNR located on the convex surface of the ZNR-paper, and conversely induced in-plane compressive strain and out-of-plane compressive strain in the ZNR located on the convex surface of the ZNR-paper.

As predicted from the change in the lattice constant, it was observed that, as $\in_b$ changes from the compressive strain to the tensile strain, a Zn—O bond length 11 along the c-axis gradually decreased while an in-plane Zn—O bond length 12 increased. In addition, as $\in_b$ changes from the compressive strain to the tensile strain, a bond angle α with respect to an axis of O—Zn—O gradually decreased from 108.84° to 108.56°, whereas, an angle β to the base increased from 110.10° to 110.36°, demonstrating the lattice deformation of the ZnO nanorods as the result of the bending.

The bending-induced anisotropic strain in the ZnO nanorod lattice suggests existence of two different Zn—O bond lengths: the Zn—O length $l_1$ along the c-axis and the Zn—O length $l_2$ in an ab-plane in the $ZnO_4$ tetrahedral unit. The ZnO in the wurtzite phase is characterized by crystallizing in a hexagonal P63*mc* space group and forming a $ZnO_4$ tetrahedron as a mirror plane perpendicular to the c-axis does not exist. The $ZnO_4$ tetrahedron under a strain condition along a specific direction is not perfect because the Zn—O bond length along the c-axis is different from that in the ab-plane, and thus, creates a net dipole moment along the c-axis. Thus, a degree of strain of the $ZnO_4$ tetrahedron, more specifically, a degree of a difference between vertical and horizontal Zn—O bond lengths, represents a level of the polarization in the ZNR. In the unstrained ZNR paper ($\in_b$=0%), the Zn—O bond length $l_1$ parallel to the c-axis is 0.010% greater than the bond length $l_2$ for three different bases, which shows a slight strain along the c-axis and a net polarization in a downward direction. The values of $l_1$ and $l_2$ gradually changed corresponding to the increase in the compression and tension $\in_b$. On tensile strained ZNR paper ($\in_b \approx 1.42\%$), $l_1$ became smaller than the other three $l_2$s by −0.17%, whereas, on compressive strained paper ($\in_b \approx -1.42\%$), $l_1$ became greater than the $l_2$s by +0.21%. This supports the anisotropic lattice deformation, which proves that the net polarization increases in the bent ZnO nanorods. D (lower) in FIG. 4 illustrates the $ZnO_4$ tetrahedral unit based on the bent state of the ZNR paper, and shows the Zn—O bond length and diversity in the polarized state. A significant out-of-plane extension resulted from the applied compression $\in_b$ moved $Zn^{2+}$ ions relatively downwards and away from a negative center of a surrounding oxygen cage, which increased a net polarization pointing to a downside. In contrast, an out-of-plane contraction resulted from the applied tension $\in_b$ moved the $Zn^{2+}$ ions in an upward direction relative to the negative oxygen center, which increased a polarization pointing to an upside. Assuming that the pyroelectricity $$p_{33} \equiv \frac{\partial P}{\partial T}$$

is defined by a change in electrical polarization ∂P during a temperature change ∂T, the increased polarized state resulted from pre-strain induced by the bending may favorably affect a pyroelectric behavior based on the subsequent temperature change.

Structural analysis confirmed that the bending behavior facilitates an in-situ arrangement along the c-axis of net electric dipoles in each $ZnO_4$ tetrahedron unit and increases the polarization level prior to the temperature change, which contributed to the improvement in the pyroelectric response under the temperature change conditions.

Experimental Example 3

Because a general body temperature remains constant at about 37° C. as a result of a homeostatic balance, a temperature of exhaled air may be considered equal to the body temperature, which is usually higher than an ambient temperature. Therefore, because cold air flows during the inhalation and warm air flows during the exhalation, a temperature flow may be created, and the temperature change over time may be accompanied by a breathing process of repeated exhalation and inhalation cycles. To investigate the pyroelectric activity of the human breathing-driven ZNR paper, a ZNR paper element was attached to the outer surface of the face mask with where the strongest air flow in a respiratory system.

Figure 5:
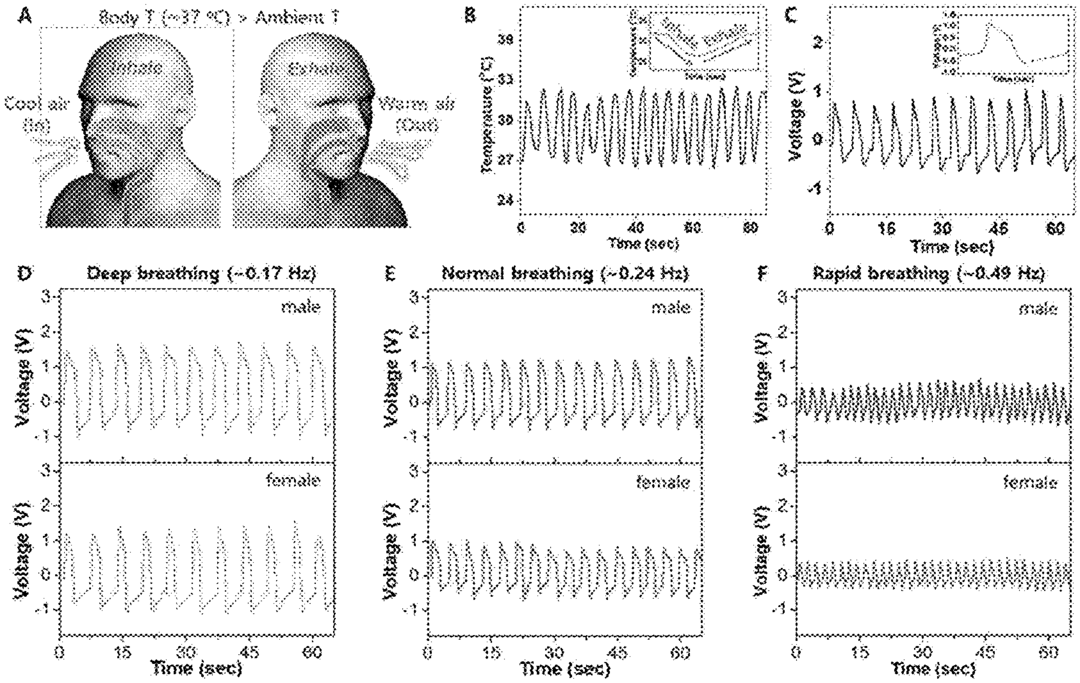
FIG. 5 shows a conceptual diagram A (upper left) for illustrating an occurrence of a temperature change corresponding to breathing for ZNR-paper integrated on a face mask, graphs B (upper middle) and C (upper right) showing a temperature change measured based on the breathing and a pyroelectric voltage corresponding thereto, and graphs D (lower left), E (lower middle), and F (lower right) showing real-time monitoring results of the pyroelectric voltage based on different types of breathing, such as deep breathing, normal breathing, and rapid breathing.

FIG. 5 shows a conceptual diagram A (upper left) for illustrating the occurrence of the temperature change corresponding to the breathing for the ZNR-paper integrated on the face mask, graphs B (upper middle) and C (upper right) showing the temperature change measured based on the breathing and the pyroelectric voltage corresponding thereto, and graphs D (lower left), E (lower middle), and F (lower right) showing real-time monitoring results of the pyroelectric voltage based on different types of breathing, such as deep breathing, normal breathing, and rapid breathing.

Referring to FIG. 5, the pyroelectric voltage may be generated in the ZNR paper by the temperature change induced based on the user's breathing cycle, and the bending stress and strain of the ZNR-paper caused in situ by attaching the ZNR paper to the face mask may cause the increase in the polarization and consequently the increase in the pyroelectric voltage.

As shown in B (upper middle) and C (upper right) in FIG. 5, the temperature change was caused by the normal breathing, and maximum and minimum temperatures reached about 32.2° C. and 27.1° C., respectively ($\Delta T \approx 5°$ C.). During the normal breathing, the corresponding pyroelectric voltage was recorded in real-time, and an average value of the voltage was determined to be 0.84 V.

A measured normal breathing-driven pyroelectric voltage was significantly higher than a voltage (0.27 V) calculated using Formula 2 based on an apparent pyroelectric constant $p_{33}$ (5.80 $\mu Cm^{-2}K^{-1}$) of the bent ZNR paper ($\in_b \approx 1.42\%$). Such voltage difference may be resulted from inaccuracy of a thermocouple sensor that measures a rapid change in an actual temperature.

In addition, to determine a detection sensitivity for the different types of breathing, such as the deep breathing, the normal breathing, and the rapid breathing, a performance of the ZNR paper-integrated-mask was investigated. The pyroelectric voltage was monitored in healthy males and females under the conditions of three types of breathing. As shown in D (lower left), E (lower middle), and F (lower right) in FIG. 5, the temperature induced by the breathing of the exhalation-inhalation was different depending on a person, but also changed differently depending on each type of breathing, and differentiable pyroelectric signals were obtained. Under the deep breathing conditions, a strong pyroelectric voltage was generated because of a sufficient time to cool or heat the ZNR paper to a certain temperature. Under the rapid breathing conditions, the ZNR paper exhibited a smaller temperature change than that under the deep breathing conditions, resulting in a weaker electrical signal. Such results clearly prove a strong dependence of the electrical signal on the breathing conditions and support the breathing-driven pyroelectric effect of the ZNR paper composite. In this respect, when combined with the pyroelectric material, the breathing may be an unrestricted and renewable source of energy. In addition, because the breathing is a metabolic process related to maintenance of life and a breathing state is able to be an important indicator of human physiological conditions, the face mask integrated with the pyroelectric ZNR paper composite may be useful for the real-time monitoring of the human breathing.

Electrical energy obtained from the temperature change in the ZNR paper composite may be converted into chemical energy, which may be referred to as a pyrocatalytic process.

Figure 6A:
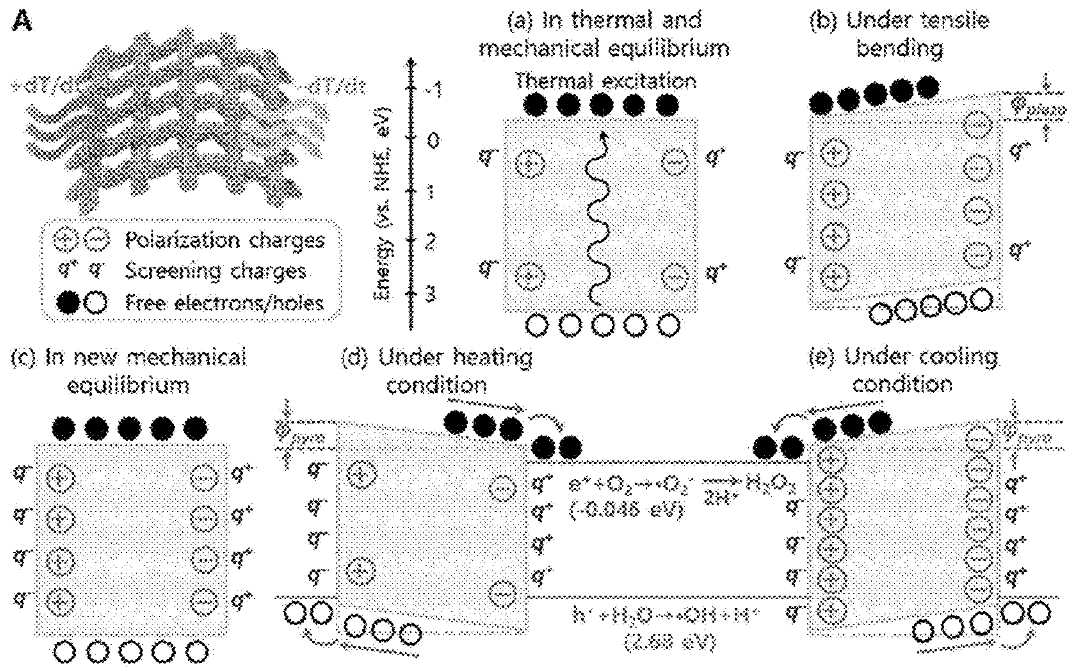
FIG. 6A is a diagram for illustrating overall mechanism of action of a pyrocatalytic activity of ZNR-paper related to a bending effect.
Figure 6B:
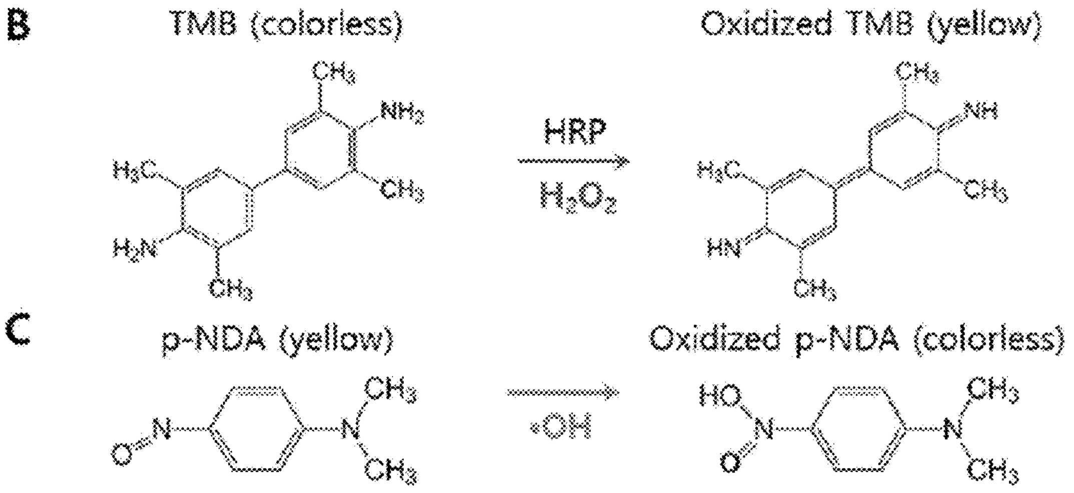
FIG. 6B is a diagram for illustrating an oxidation reaction B of TMB (3,3,5,5-tetramethylbenzidine) by $H_2O_2$ and an oxidation reaction of p-NDA (p-nitrosodimethylaniline) by hydroxyl radical (·OH)
Figure 6C:
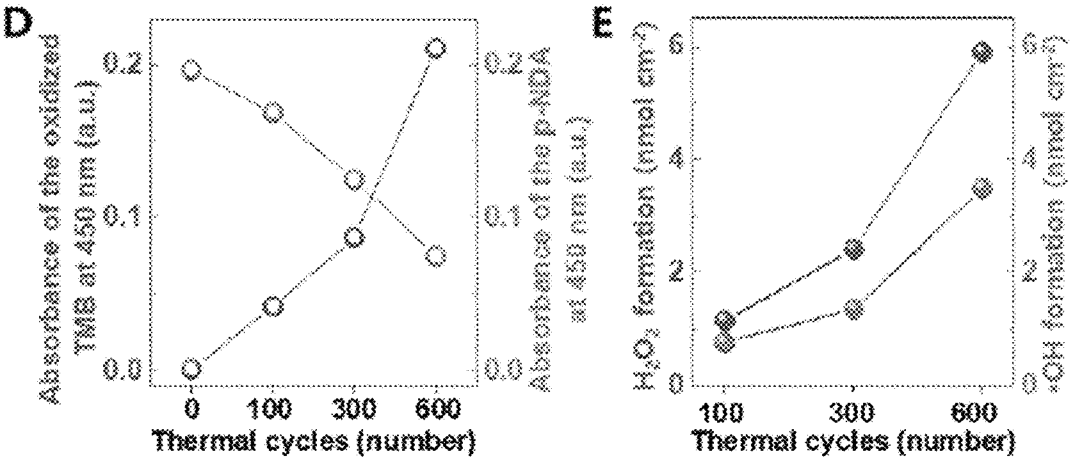
FIG. 6C shows graphs showing an absorbance change D at 450 nm of newly produced TMB and reactant p-NDA based on the number of thermal cycles and quantitative measurement results E of $H_2O_2$ and ·OH.
Figure 6D:
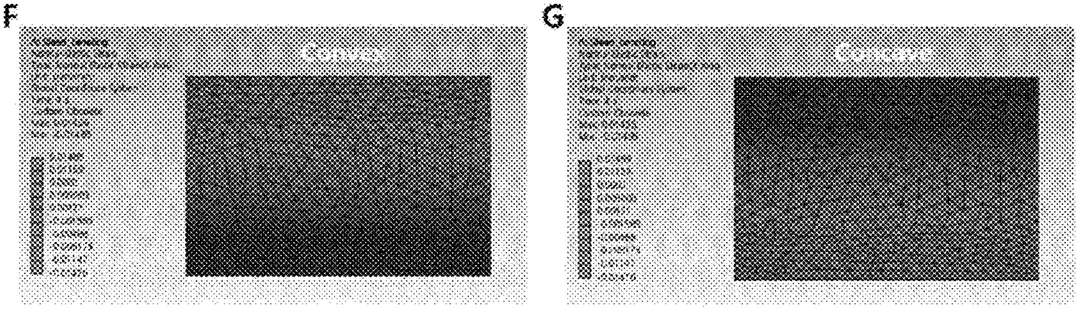
FIGS. 6D and 6E are diagrams showing strain field distribution and strain line profiles on a convex surface F (left of FIG. 6D) and H (left of FIG. 6E) and on a concave surface G (right of FIG. 6D) and I (right of FIG. 6E) of the bent ZNR-paper composite.
Figure 6E:
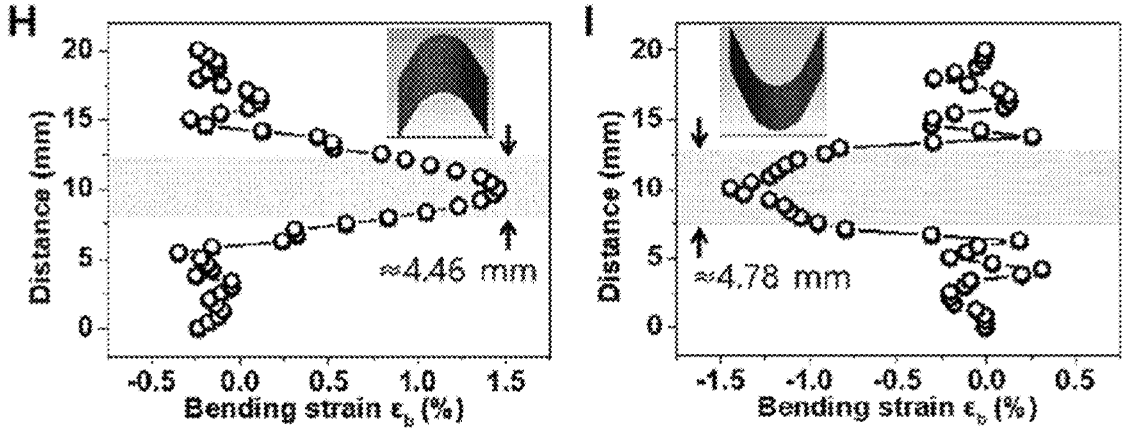
Figure 6F:
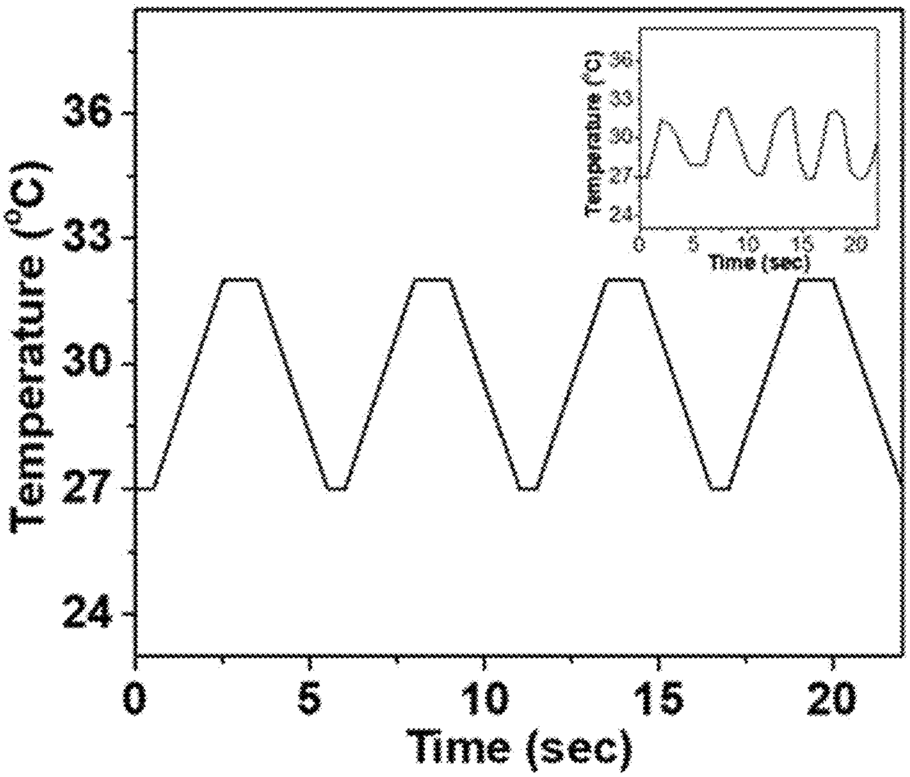
FIG. 6F is a graph showing a programmed temperature flow for a thermal cycle similar to a breathing-induced cycle.

FIG. 6A is a diagram for illustrating overall mechanism of action of a pyrocatalytic activity of the ZNR-paper related to the bending effect, FIG. 6B is a diagram for illustrating an oxidation reaction B (upper) of TMB (3,3,5,5-tetramethylbenzidine) by $H_2O_2$ and an oxidation reaction (lower) of p-NDA (p-nitrosodimethylaniline) by hydroxyl radical (·OH), FIG. 6C shows graphs showing an absorbance change D (left) at 450 nm of newly produced TMB and reactant p-NDA based on the number of thermal cycles and quantitative measurement results E (right) of $H_2O_2$ and ·OH, FIGS. 6D and 6E are diagrams showing strain field distribution and strain line profiles on the convex surface F (left of FIG. 6D) and H (left of FIG. 6E) and on the concave surface G (right of FIG. 6D) and I (right of FIG. 6E) of the bent ZNR-paper composite, and FIG. 6F is a graph showing a programmed temperature flow for a thermal cycle similar to the breathing-induced cycle.

Referring to FIGS. 6A to 6F, in thermal and mechanical equilibrium conditions (i.e., constant temperature and pressure), the ZnO nanorod crystals in the wurtzite phase contain spontaneously polarizing charges at both distal ends thereof, which may be fully compensated for by screening charges in a surrounding medium. During the tensile bending, the $ZnO_4$ tetrahedron unit in a ZnO nanorod crystal structure was deformed along the c-axis, which may cause accumulation of piezoelectrically induced polarized charges across the bent ZnO nanorods. Similarly, under the compressive bending conditions, the piezoelectrically induced polarized charges accumulated in an opposite manner to those during the tensile bending.

A piezoelectric potential $\phi_{piezo}$ was easily weakened to zero under the conditions of no strain change (maintaining the bent state), and thus, a new balance was achieved between the polarization and the screening charges. The bent ZnO nanorods were more polarized than the undeformed ZnO nanorods because of the piezoelectrically induced polarization charge, which may contribute to inducing strong polarization in response to the temperature change, thus leading to high pyroelectricity and pyrocatalysis.

Thereafter, when the thermal equilibrium is disrupted by heating of the ZnO nanorods, the dipoles lose the orientation thereof due to increased thermal vibrations, which may change the level of the polarized state. In contrast, decreasing the temperature favors the dipole orientation because of reduced vibration, which causes a change in the polarization. Such change in the polarization simultaneously moves intrinsic free carriers in opposite directions, enhances the pyroelectric potential $\phi_{pyro}$, and tilts the electrical band structure of the ZnO nanorods. However, unlike the movable free carriers, surface-polarized-charges are bound inside the ZnO nanorod crystals, which inhibits the surface-polarized-charges from directly participating in the ROS generating redox reaction. Instead, the surface-polarized-charges assist the ROS generation by tilting the electromagnetic band edge by dragging a conduction band CB and a valance band VB closer to a redox potential level of the ROS. Regarding redox potential energy for the ROS generation, a specific ROS may be generated when the ZNR paper pyrocatalyst has a suitable electromagnetic band arrangement. Free electrons and holes inside the semiconductor ZnO nanorods generated by thermal activation (T>0) without the doping may directly contribute to the ROS generation. Therefore, the pyroelectric potential-induced tilting of the CB and the VB may facilitate reaction of intrinsic electrons and holes with surrounding oxygen ($O_2$) and water ($H_2O$), and may promote the production of ROS and ·OH from $H_2O$. Because a degree of energy band tilt is proportional to the pyroelectric potential, the high pyroelectricity induced by pre-strain may significantly promote the ROS generation. For example, the ROS of $\cdot O_2^-$ and $H_2O$ may be generated under heating/cooling conditions in the ZNR paper pyrocatalyst. Because a CB edge (−0.16 eV vs. NHE) of the ZnO nanorods has a more negative value than a redox potential (−0.046 eV vs. NHE) of $O_2/\bullet_2^-$, the intrinsic free electrons may react with surrounding $O_2$ molecules to form the ROS of $\cdot O_2$ (superoxide radical), which may be easily converted to highly stable $H_2O_2$ via a $$2\cdot O_2^- + 2H^+ \rightarrow H_2O_2$$

reaction. In addition, because of the electromagnetic band tilting of the ZnO nanorods, the CB edge of the ZnO nanorods is located close to the redox potential of $O_2/\cdot O_2^-$ where the formation of $\cdot O_2^-$ and $H_2O_2$ is additionally promoted. Similarly, a VB edge (3.53 eV vs. NHE) of the ZnO nanorods has a more positive value than a redox potential (2.68 eV vs. NHE) of $\cdot OH/H_2O$, and approaches the $\cdot OH/H_2O$ level because of the pyroelectric potential-induced band tilting. This may facilitate the oxidation of $H_2O$ by holes in the VB, and as a result, OH (hydroxyl radical) may be effectively generated.

The human breathing-driven ROS formation in the ZNR-paper may be demonstrated in terms of $H_2O_2$ and ·OH. Before the temperature change, an effect of the bending ($\in_b \approx 1.42\%$) of the ZNR paper caused as the ZNR paper is attached to the face mask was simulated. The bent ZNR paper was then exposed to the temperature flow programmed for 100, 300, and 600 thermal cycles similar to the breathing-induced cycles shown in FIG. 6F. $H_2O_2$ was detected based on enzymatic reduction of $H_2O_2$ in the presence of a HRP (horseradish peroxidase) catalyst and a TMB (3,3,5,5-tetramethylbenzidine) substrate (see FIG. 6B). ·OH was measured using p-NDA (p-nitrosodimethylaniline) molecules as a selective ·OH scavenger (see FIG. 6C).

The p-NDA was decolored from yellow to be transparent after ·OH quenching, whereas the TMB became yellow after $H_2O_2$ reduction. Therefore, amounts of $H_2O_2$ and ·OH were determined using a color change method by measuring adsorption of oxidized TMB (fresh in solution) and residual p-NDA (a left side in solution) at 450 nm. As shown in D (left of FIG. 6C) in FIG. 6, an absorption value of the oxidized TMB gradually increased as the number of thermal cycles increased, whereas an opposite change tendency was observed for the residual p-NDA. The amounts of the oxidized TMB and the residual p-NDA were calculated using molecular extinction coefficients, $\varepsilon_{oxidized\ TMB}=5.9\times 10^4\ M^{-1}\ cm^{-1}$ and $\varepsilon_{p\text{-}NDA}=3.43\times 10^4\ M^{-1}\ sm^{-1}$ thereof based on the Beer-Lambert Law, which establishes a linear relationship between absorption and molality of an analyte. In addition, the amounts of $H_2O_2$ and ·OH were quantified based on a ROS scavenger reaction where oxidation of a reactant of the TMB and the p-NDA occurs at a stoichiometric ratio of 1(ROS):1(reactant) yielding 1 mole of an oxidation product. As shown in E (right of FIG. 6C) in FIG. 6, the bent ZNR paper composite released $H_2O_2$ and ·OH in amounts of 5.90 nmol and 3.49 nmol, respectively, per unit area (1 $cm^2$) of the composite by 600 thermal cycles, which corresponds to a thermal durability of only 1 hour. Because of a longer lifetime of $\cdot O_2^-$ ($\approx 10^{-6}$ see) and $H_2O_2$(~hour-days) compared to that of ·OH ($\approx 10^{-9}$ sec), $H_2O_2$ of a relatively greater amount comparted to that of 0H was detected. The ROS scavenger test results shows that the face mask integrated with ZNR paper may be effectively used as the pyrocatalyst to generate the ROS of the $H_2O_2$ and the ·OH without extra effort during the normal exhalation-inhalation cycle.

In addition, based on a strain field distribution on the ZNR-paper composite, an effective area for generating the ROS on the bent ZNR paper composite was evaluated. A magnitude of the applied strain varied depending on a position in a length direction of the substrate, and a central portion was significantly deformed, playing an important role in the ROS generation. As a result of simulating the strain field distribution on the bent ZNR-paper composite ($\in_b$=1.42%) using finite element analysis software, as shown in F (left of FIG. 6D) and G (right of FIG. 6D) in FIG. 6, a maximum bending strain was applied to the convex portion, and the concave composite surface was evaluated to have values of +1.49% (tensile, red) and −1.48% (compressive, blue), which were close to the calculated value of ±1.42%. The maximum bending strain was induced at the central area of the substrate, and the magnitude of the bending strain gradually decreased toward a distal end area. As shown in line profiles of H (left of FIG. 6E) and I (right of FIG. 6E) in FIG. 6, substrate areas equal to or greater than 70% of the maximum value of the induced strain were calculated to be 89.2 $mm^2$ (the convex surface) and 95.6 $mm^2$ (the concave surface), which accounted for 22.3% and 23.9% of a total composite area (400 $mm^2$), respectively.

Experimental Example 4

It is determined that the ZNR paper-integrated-face mask may cause the increased polarization induced by the bending, and thus, perform the effective ROS generation, and as a result, may exhibit excellent sterilization effect. To prove a potential sterilization activity of the ZNR paper-integrated-face mask, bacterial and viral species were cultured with the bent ZNR paper ($\in_b$≈1.42%), and then were placed in pre-programmed temperature change conditions similar to the normal breathing conditions for the 600 thermal cycles (duration=1 h).

Antibacterial Activity

The antibacterial activity of the ZNR paper was evaluated using two pathogenic Gram-negative bacteria, *Salmonella enteritidis* (*S. enteritidis*) and *Acinetobacter baumannii* (*A. baunannii*), as model cells. To determine an effect of a pyrocatalyst-driven antibacterial activity of the ZNR paper, the cells were exposed for a certain period of time to three different environments of (1) temperature-changing-paper ("paper+ΔT," control 1), (2) temperature-constant-ZNR paper ("ZNR paper," control 2), and (3) temperature-changing-ZNR paper ("ZNR paper+ΔT," control 3). After 1 hour of treatment, growth and proliferation of the *S. enteritidis* and *A. baumannii* cells were assessed by counting the number of bacterial colony forming units (CFU) on agar plates.

Figure 7A:
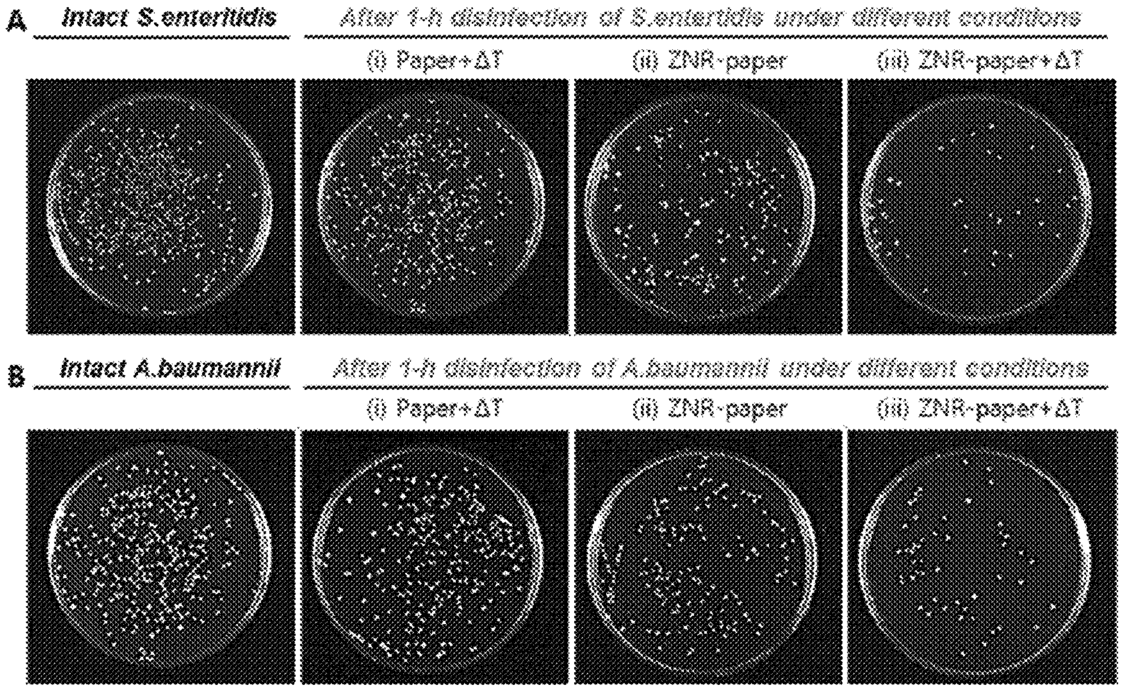
FIGS. 7A and 7B respectively show bacterial community images of *S. enteritidis* A (upper of FIG. 7A) and C (left of FIG. 7B) and *A. baumannii* B (lower of FIG. 7A) and D (right of FIG. 7B) before and after sterilization for 1 hour under three different environments, and graphs showing the measured bacterial community numbers C (left of FIG. 7B) and D (right of FIG. 7B)
Figure 7B:
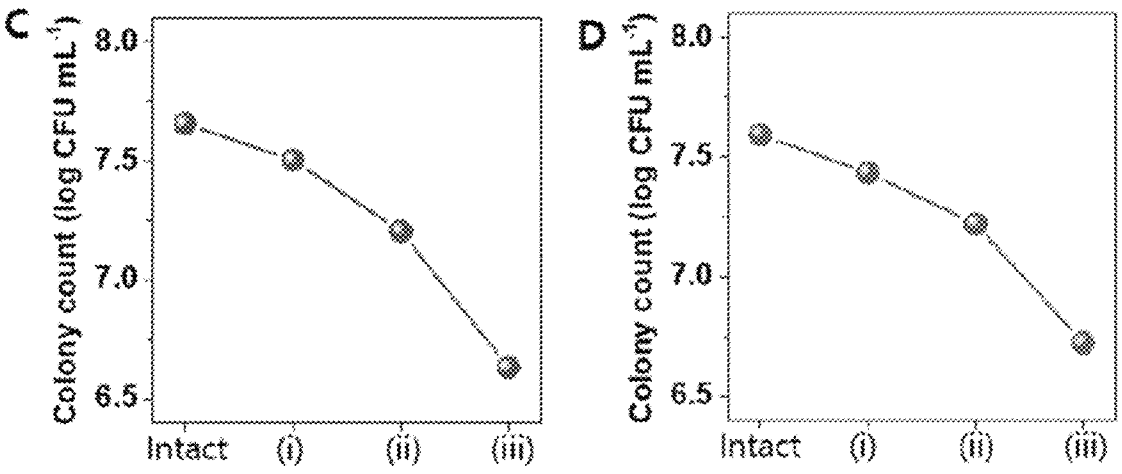
Figure 7C:
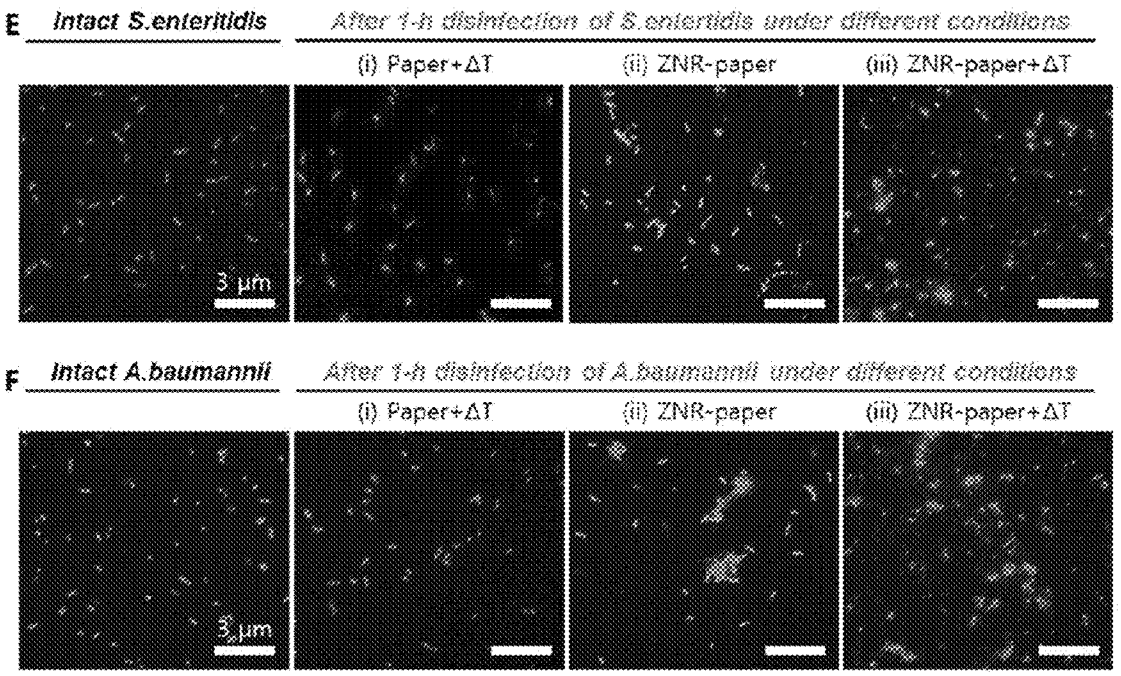
FIG. 7C shows fluorescence images of the *S. enteritidis* E (upper) and the *A. baumannii* F (lower) before and after the sterilization for 1 hour under the three different environments.
Figure 7D:
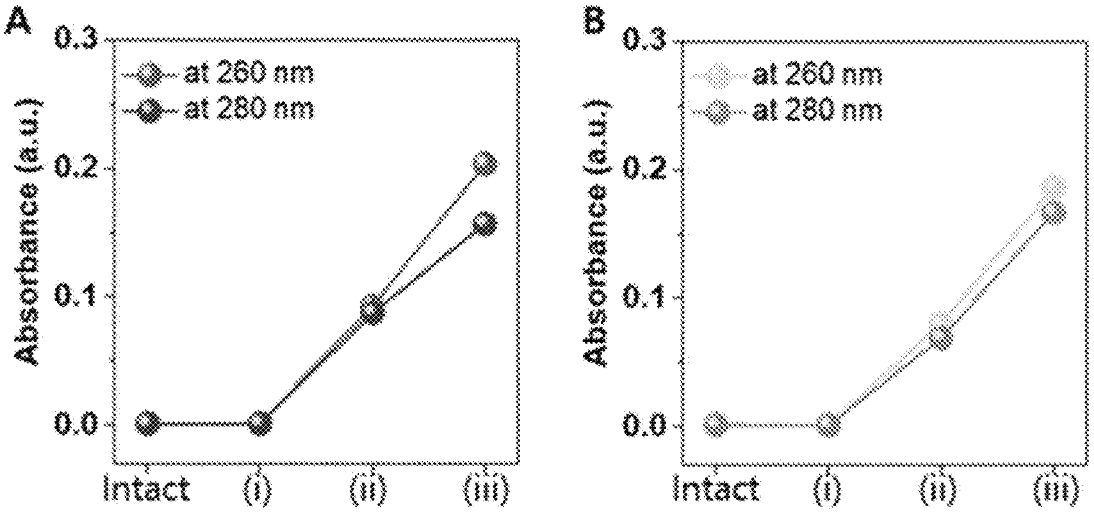
FIG. 7D shows graphs showing measurement results of absorbance at 260 nm and 280 nm associated with characteristic peaks of nucleic acid and protein, respectively, for cell supernatant containing the nucleic acid and the protein released from the *S. enteritidis* and the *A. baumannii.*

FIGS. 7A and 7B respectively show bacterial community images of the *S. enteritidis* A (upper of FIG. 7A) and C (left of FIG. 7B) and the *A. baumannii* B (lower of FIG. 7A) and D (right of FIG. 7B) before and after sterilization for 1 hour under three different environments, and graphs showing the measured bacterial community numbers C (left of FIG. 7B) and D (right of FIG. 7B), FIG. 7C shows fluorescence images of the *S. enteritidis* E (upper) and the *A. baumannii* F (lower) before and after the sterilization for 1 hour under the three different environments, and FIG. 7D shows graphs showing measurement results of absorbance at 260 nm and 280 nm associated with characteristic peaks of nucleic acid and protein, respectively, for cell supernatant containing the nucleic acid and the protein released from the *S. enteritidis* and the *A. baumannii.*

Referring to FIGS. 7A to 7D, a slight decrease in the number of CFUs was observed in both cells under the environment of "paper+ΔT," which is resulted from the fiber network of the paper for trapping bacterial cells inside the pores. In both cells under the "ZNR paper+ΔT" environment with the temperature change (ΔT) and the "ZNR-paper" environment without the temperature change (ΔT), an additional decrease in the number of CFUs was achieved compared to under the "paper+ΔT" environment. This is because the ZnO nanorods may not only penetrate into the cells, damage protein and DNA, destroy a mitochondrial redox level, but also function as an antibacterial agent by $Zn^{2+}$ ions released from partial dissolution of the ZnO nanorods. In addition, mechanical destruction of a cell membrane and the penetration may occur by sharp edges of the ZnO nanorods, and accordingly, cell death may be caused, so that the ZnO nanorods may remarkably prevent spread of the bacteria even at the constant temperature with no temperature change (ΔT). In one example, growth and spread of the two cells were significantly inhibited under the environment of "ZNR paper+ΔT" with the temperature change (ΔT) compared to under the environment of "ZNR-paper" without the temperature change (ΔT), which is resulted from the ROS generated by the pyrocatalytic function of the ZnO nanorods under the environment of "ZNR paper+ΔT." Under the environment of "ZNR paper+ΔT," the number of CFUs was reduced by 90.5% for the *S. enteritidis* and by 86.5% for the *A. baumannii* cells. Such results indicate that the ZNR-paper with the pyrocatalytic activity has excellent antibacterial activity.

In one example, as shown in FIG. 7C, the cell damage and death were visualized by bacterial fluorescent staining using acridine orange (AO), a nucleic acid-selective staining dye. The cell-permeable AO dye reacts with double-stranded DNA (deDNA) via intercalation using electrostatic interaction and single-stranded DNA (ssDNA) or RNA, and emits green fluorescence (526 nm) and red fluorescence (650 nm). AO-stained live cells with intact DNA emit the green fluorescence, whereas dead cells with decayed DNA emit the red fluorescence. As shown in FIG. 7C, the *S. enteritidis* and the *A. baumannii* exhibited the green fluorescence before the sterilization, and remained intact even after cultivation for 1 hour in the "paper+ΔT" environment. Such results indicate that the paper only functions to trap the cells and is not effective in killing the cells. On the other hand, the ZnO nanorods appeared to affect cell viability, as indicated by the red fluorescence signal emitted from the dead cells. In addition, when the cells were cultured for 1 hour in the environment of "ZNR paper+ΔT" with the temperature change, a remarkably high ratio of the red fluorescence was observed, which shows that the ZNR paper is effective in killing the bacteria based on the pyrocatalytically generated ROS.

As shown in FIG. 7D, the cell death was further investigated by measuring the absorption at 260 nm and 280 nm associated with the characteristic peaks of the nucleic acid and the protein, respectively, for the cell supernatant containing the nucleic acid and the protein released. A DNA and protein leakage from the cells occurred under the environments of "ZNR paper" and "ZNR paper+ΔT," which confirms that the paper itself has little effect on cell integrity and death. The further increase of the released DNA and protein was achieved under the environment of "ZNR paper+ΔT"

compared to the environment of "ZNR paper" under the constant temperature conditions, indicating a significant effect of the temperature-changing-ZNR paper on the antibacterial process.

Antiviral Activity

The antiviral activity of the ZNR paper was evaluated using SE2 phage and ABA phage as model viruses. The SE2 phage is a lytic phage whose host is the *S. enteritidis*, is composed of non-enveloped viruses, and is classified as a Siphoviridae family with icosahedral DNA viruses. The ABA phage is an *A. baumannii*-specific phage with lytic activity belonging to a Myoviridae family, which is composed of viruses with non-enveloped DNA.

It has been reported that, compared to enveloped viruses, the non-enveloped viruses are more resistant to extreme environments such as detergent and heat. Therefore, the non-enveloped SE2 and ABA phages may be suitable models to evaluate sensitivity to the temperature-changing-ZNR paper. To evaluate an effect of the pyrocatalytically generated ROS on the antiviral activity, both phages were exposed, for a certain period of time, to the three different environments: (1) "paper+ΔT," (2) "ZNR paper," and (3) "ZNR paper+ΔT."

Figure 8A:
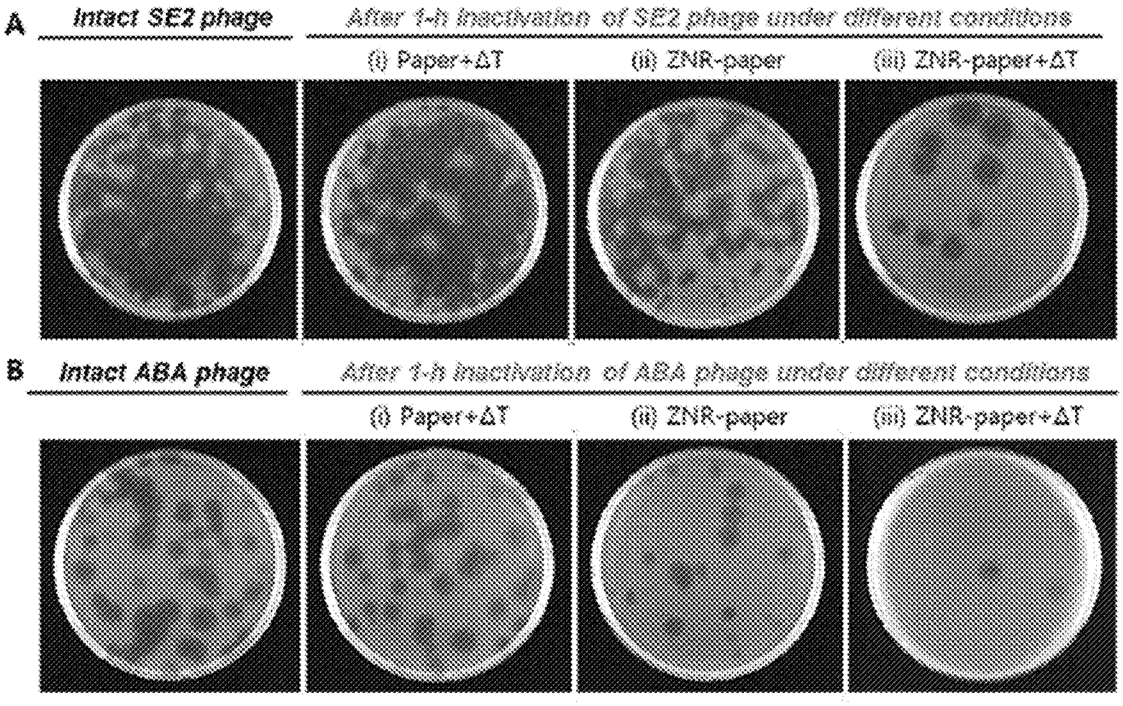
FIGS. 8A and 8B respectively show bacterial community images of SE2 phages A (upper of FIG. 8A) and C (left of FIG. 8B) and ABA phages (B (lower of FIG. 8A) and D (right of FIG. 8B)) before and after sterilization for 1 hour under three different environments, and graphs showing the measured bacterial community numbers C (left of FIG. 8B) and D (right of FIG. 8B)
Figure 8B:
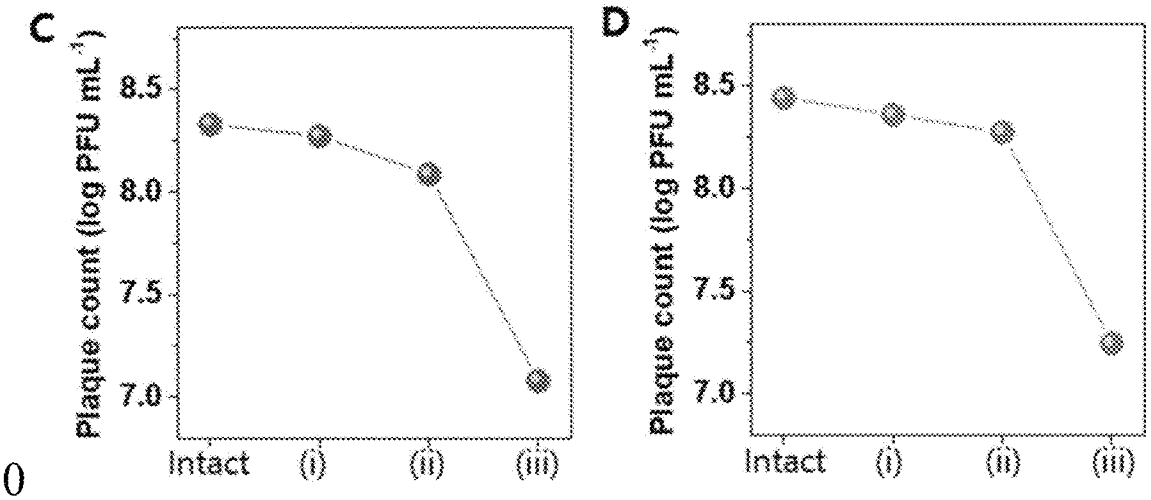
Figure 8C:
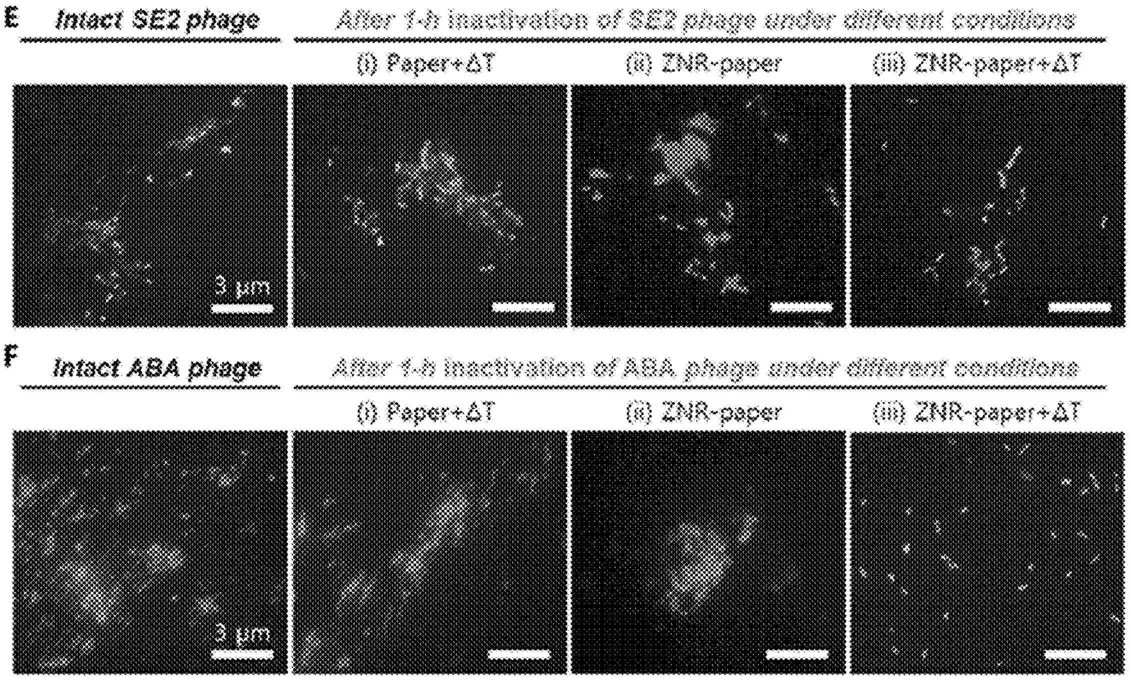
FIG. 8C shows fluorescence images of the SE2 phages E (upper) and the ABA phages F (lower) before and after the sterilization for 1 hour under the three different environments.

FIGS. 8A and 8B respectively show bacterial community images of the SE2 phages A (upper of FIG. 8A) and C (left of FIG. 8B) and the ABA phages (B (lower of FIG. 8A) and D (right of FIG. 8B)) before and after sterilization for 1 hour under three different environments, and graphs showing the measured bacterial community numbers C (left of FIG. 8B) and D (right of FIG. 8B), and FIG. 8C shows fluorescence images of the SE2 phages E (upper) and the ABA phages F (lower) before and after the sterilization for 1 hour under the three different environments.

Referring to FIGS. 8A to 8C, the two phages were significantly less sensitive to the "paper+ΔT" than the bacterial cells, which indicates that the paper is ineffective in trapping the phages inside the pores due to a significantly smaller size (about 200 nm) of the phages compared to that (1000 nm) of the bacterial cells. The lytic activity of the two phages was affected in the "ZNR paper" with no temperature change, which is because of the $Zn^{2+}$ ions that may be released from partial dissolution of the ZnO nanorods and may damage capsid protein of the phages. In addition, a radical reduction in the plaque number for both phages indicated a high vulnerability of the phages to the ROS generation conditions (e.g., the "ZNR paper+ΔT"). Under the "ZNR paper+ΔT" environment, the number of PFUs was reduced by 94.4% for the SE2 phage and by 93.6% for the ABA phage. It was reported that viral particles are more sensitive to the ROS than the bacteria because the ROS may induce cross-linking of the capsid proteins of the phages and directly impair an ability of the phages to bind to a host surface. Such results prove that, in the case of antiviral activity, the ZNR paper capable of generating the ROS by the pyrocatalytic function has the excellent antiviral activity.

A viral sterilization degree was visualized by the bacterial fluorescence staining method using the AO dye. To evaluate degrees of sterilization and inactivation of the phages, the phage samples were subjected to a sterilization process for 1 hour, then cultured with respective host bacteria, and then stained with the AO dye. Cells with phage-damaged DNA emitted the red fluorescence, whereas intact cells emitted the blue fluorescence. As shown in FIG. 8C, the intact SE2 phage and ABA phage completely lysed the respective host cells of the *S. enteritidis* and the *A. baumannii*, which may demonstrate the lytic activity thereof against the host cells. Even after the cultivation under the "paper+ΔT" environment, the phages were found to readily attack and lyse the host cells. In contrast, blue light was observed under the environment with the ZNR paper, which proves that some cells survive because the phages have lost the lytic activity thereof against the host cells.

In addition, most of the cells were found to survive after the cultivation with the phages sterilized under the "ZNR paper+ΔT" environment. Such antiviral test results indicate that the temperature-changing-ZNR paper may be effectively used for the sterilization or the inactivation of the viruses.

Although the present disclosure has been described with reference to the preferred embodiment, those skilled in the art will understand that the present disclosure may be modified and changed in various ways without departing from the spirit and scope of the present disclosure described in the claims below.

What is claimed is:

1. A bioprotective composite material comprising:

a fiber network support;

a seed layer for covering a surface of the fiber network support; and pyroelectric nanostructures protruding from the seed layer and generating an instantaneous pyro-potential by a temperature change, wherein the fiber network support contains a fabric of polymer fibers.

2. The bioprotective composite material of claim 1, wherein the polymer fibers are made of a polyamide-based, polyimide-based, polypropylene-based, or polyethylene-based polymer material having hydrophilicity.

3. The bioprotective composite material of claim 1, wherein the seed layer is made of an inorganic material containing a metal element of a material constituting the pyroelectric nanostructures, and covers a surface of the polymer fibers constituting the fiber network support.

4. The bioprotective composite material of claim 3, wherein each of the pyroelectric nanostructures has a shape of a nanorod oriented in a direction protruding from the seed layer.

5. The bioprotective composite material of claim 4, wherein each of the pyroelectric nanostructures contains zinc oxide having a non-centrosymmetric hexagonal wurtzite phase crystal structure.

6. The bioprotective composite material of claim 5, wherein the zinc oxide includes a $ZnO_4$ tetrahedron unit having a Zn—O bond length in an in-plane direction of the seed layer and a Zn—O bond length in an out-of-plane direction of the seed layer different from each other to generate a net dipole moment along the out-of-plane direction.

7. The bioprotective composite material of claim 5, wherein the pyroelectric nanostructures have an average diameter in a range from 50 to 400 nm and an average length in a range from 600 to 1500 nm.

8. A face mask comprising:

a mask; and a bioprotective composite material coupled to the mask and including a fiber network support, a seed layer for covering a surface of the fiber network support, and pyroelectric nanostructures protruding from the seed layer and generating an instantaneous pyro-potential by a temperature change.

9. The face mask of claim 8, wherein the pyro-potential is generated by the temperature change caused by breathing of a user wearing the face mask, wherein the pyro-potential promotes a reaction to generate reactive oxygen species (ROS) from surrounding water, water vapor, or oxygen.

10. The face mask of claim 8, wherein the fiber network support contains a fabric of polymer fibers, wherein the seed layer is made of an oxide or a nitride containing a metal element of a material constituting the pyroelectric nanostructures and covers a surface of the polymer fibers, wherein each of the pyroelectric nanostructures has a shape of a nanorod oriented in a direction protruding from the seed layer.

11. The face mask of claim 10, wherein the pyroelectric nanostructures have an average diameter in a range from 50 to 400 nm and an average length in a range from 600 to 1500 nm.

12. The face mask of claim 10, wherein each of the pyroelectric nanostructures contains zinc oxide having a non-centrosymmetric hexagonal wurtzite phase crystal structure.

13. The face mask of claim 12, wherein the zinc oxide includes a $ZnO_4$ tetrahedron unit having a Zn—O bond length in an in-plane direction of the seed layer and a Zn—O bond length in an out-of-plane direction of the seed layer different from each other to generate a net dipole moment along the out-of-plane direction.

14. The face mask of claim 13, wherein deformation of the bioprotective composite material based on a facial curve of a user wearing the face mask causes lattice deformation of the pyroelectric nanostructures to increase the dipole moment of the zinc oxide.

* * * * *